(12) United States Patent
Block

(10) Patent No.: US 12,178,599 B2
(45) Date of Patent: Dec. 31, 2024

(54) SYSTEMS AND METHODS FOR ACCURATE MEASUREMENT OF PROPRIOCEPTION

(71) Applicant: Indiana University Research and Technology Corporation, Indianapolis, IN (US)

(72) Inventor: Hannah J. Block, Bloomington, IN (US)

(73) Assignee: Indiana University Research and Technology Corporation, Bloomington, IN (US)

( * ) Notice: Subject to any disclaimer, the term of this patent is extended or adjusted under 35 U.S.C. 154(b) by 1436 days.

(21) Appl. No.: 16/324,228

(22) PCT Filed: Aug. 11, 2017

(86) PCT No.: PCT/US2017/046486
§ 371 (c)(1),
(2) Date: Feb. 8, 2019

(87) PCT Pub. No.: WO2018/031878
PCT Pub. Date: Feb. 15, 2018

(65) Prior Publication Data
US 2019/0216388 A1    Jul. 18, 2019

Related U.S. Application Data

(60) Provisional application No. 62/373,613, filed on Aug. 11, 2016.

(51) Int. Cl.
*A61B 5/00* (2006.01)
*A61B 5/11* (2006.01)

(52) U.S. Cl.
CPC .......... *A61B 5/4538* (2013.01); *A61B 5/1121* (2013.01); *A61B 5/4082* (2013.01);
(Continued)

(58) Field of Classification Search
CPC ... A61B 5/1121; A61B 5/1124; A61B 5/4538; A61B 5/4082; A61B 5/702; A61B 5/743; A61B 5/224; A61B 5/16; G09B 19/003
See application file for complete search history.

(56) References Cited

U.S. PATENT DOCUMENTS 4,836,531 A     6/1989  Niks
6,155,993 A    12/2000  Scott
(Continued)

OTHER PUBLICATIONS

Hoseini, N., Sexton, B. M., Kurtz, K., Liu, Y., & Block, H. J. (2015). Adaptive staircase measurement of hand proprioception. PLoS One, 10(8), e0135757. (Year: 2015).*
(Continued)

*Primary Examiner* — Devin B Henson
*Assistant Examiner* — Evelyn Grace Park
(74) *Attorney, Agent, or Firm* — Faegre Drinker Biddle & Reath LLP

(57) ABSTRACT

Stands for measuring proprioception comprising a hand layer comprising one or more vertically offset portions configured to ensure proper placement of a patient's hand in a predetermined position, a top cover coupled to the hand layer, wherein the top cover is designed to obscure the patient's view of the patient's hand, and a support element coupled to the hand layer and configured to support the hand layer at a predetermined angle are disclosed. Methods for measuring proprioception are also disclosed.

9 Claims, 20 Drawing Sheets

(52) U.S. Cl.
CPC .............. *A61B 5/702* (2013.01); *A61B 5/743* (2013.01); *A61B 5/1124* (2013.01)

(56) References Cited

U.S. PATENT DOCUMENTS

2007/0060445 A1   3/2007   Reinkensmeyer et al.
2008/0108883 A1   5/2008   Scott et al.

OTHER PUBLICATIONS

Barkley, Victoria, et al. "Reach adaptation and proprioceptive recalibration following terminal visual feedback of the hand." Frontiers in Human Neuroscience 8 (2014): 705. (Year: 2014).*

Barkely, Victoria, et al. "Reach adaptation and proprioceptive recalibration following terminal visual feedback of the hand." Frontiers in Human Neurscience 8 (2014): 705. pp. 1-11. (Year: 2014).*

International Search Report and Written Opinion issued by the ISA/US Commissioner for Patents, dated Dec. 11, 2017, for International Application No. PCT/US2017/046486.

Hoseini, Najmeh et al., Adaptive Staircase Measurement of Hand Proprioception; Aug. 14, 2015; PLoS ONE 10(8): e0135757; doi:10.1371/journal.pone.0135757.

* cited by examiner

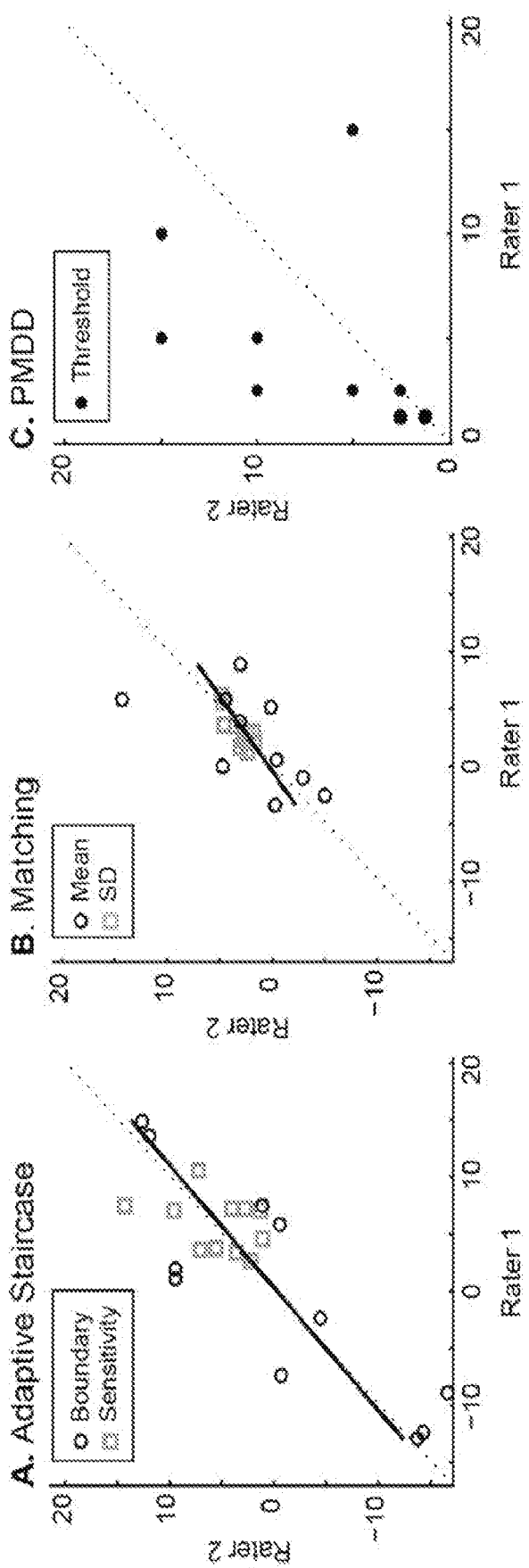

| Age | Years since stroke | Description | Proprioception | | | | Tactile | | Motor | | |
|---|---|---|---|---|---|---|---|---|---|---|---|
| | | | Tablet Degrees | PMDD Degrees | FM thumb Score | FM index Score | Fine touch Level | | FM UL Score | BBT # blocks | MRC Score |
| 55 | 3.4 | Anterior L MCA ischemic | -21 | 1.25 | ? | ? | 3.61 | 6.65 | 64 | 76 | 5 4 |
| 85 | 2.5 | Acute infarction of L thalamus | 7 | 2.5 | ? | ? | 3.61 | 3.61 | 55 | 17 | 5 5 |
| 56 | 10.0 | L pontine ischemic cerebral infarct s/p basilar occlusion | -9 | 5 | 2 | 2 | 4.31 | 3.61 | 64 | 50 | 5 5 |
| 87 | 2.0 | Unknown | 19 | 10 | 2 | 2 | 3.61 | 6.65 | 62 | 34 | 5 5 |
| 43 | 7.4 | Unknown | -6 | 2.5 | 2 | 1 | 3.61 | 6.65 | 64 | 68 | 5 5 |
| 82 | 2.9 | Right lacunar | -11 | 6 | 1 | 2 | 2.83 | 3.61 | 51 | 39 | 5 6 |
| 55 | 3.4 | Perioperative hemorrhagic event | 1 | 5+ | 2 | 2 | 4.31 | 5.07 | 64 | 57 | 5 5 |
| 53 | 2.5 | Unknown | -9 | 1.25 | 2 | 2 | 3.61 | 3.61 | 18 | 0 | 5 0 |
| 54 | 1.3 | Right MCA CVA | -25 | 1.25 | 2 | 2 | 3.61 | 3.61 | 60 | 53 | 5 5 |
| 31 | 13.3 | Unknown | -9 | 5 | 2 | 2 | 4.31 | 2.83 | 46 | 45 | 5 6 |
| 69 | 7.1 | Right MCA CVA | -18 | 2.5 | 2 | 1 | 3.61 | 3.61 | 46 | 6 | 5 0 |
| 66 | 1.1 | L MCA ischemic, L basal ganglia hemorrhagic | -11 | 10 | 2 | 2 | 3.61 | 3.61 | 8 | 42 | 5 4 |
| | | | 5 | 10 | 2 | 2 | 3.61 | 3.61 | 51 | 1 | 5 5 |
| | | | | | | | | | 47 | 0 | 5 5 |
| | | | | | | | | | 57 | 23 | 5 5 |
| | | | | | | | | | 47 | 30 | 5 5 |
| | | | | | | | | | 64 | 32 | 5 5 |

FIG. 17

SYSTEMS AND METHODS FOR ACCURATE MEASUREMENT OF PROPRIOCEPTION

CROSS-REFERENCE TO RELATED APPLICATIONS

The present application is a U.S. national stage under 35 U.S.C. § 371 of International Application No. PCT/US2017/046486, filed on Feb. 11, 2017, which claims priority from and the benefit of U.S. Provisional Application No. 62/373,613, filed on Aug. 11, 2016, the entire disclosures each of which is hereby expressly incorporated herein by reference in its entirety.

FIELD OF THE DISCLOSURE

This disclosure relates systems and methods for accurately measuring the proprioception of patients. More specifically, this disclosure relates to passive systems and passive methods for accurately measuring the proprioception of patients.

BACKGROUND

To interact efficiently with the environment, for example reaching to pick up a mug, a sense of where our hand is and how it is moving is needed. This arises from the proprioceptive senses, including static position sense, movement sense or kinesthesia, and sense of force or heaviness, among others. Proprioception is important for accurate movement, but is frequently impaired following a stroke. This has important functional consequences, including poor recovery of mobility, ability to function in daily activities, and impaired motor learning.

Proprioceptive deficits are thought to play a role in the motor impairments associated with other conditions as well, including multiple sclerosis, Parkinson's and Huntington's diseases, fall risk in the elderly, concussion, autism, and chronic pain. Hand/finger proprioception is particularly important because of the role it plays in manual dexterity and associated tasks of daily living.

To manage therapy plans and reevaluate patients after interventions, clinicians often assess proprioceptive acuity. One conventional clinical test is passive movement direction discrimination (PMDD), which measures movement sense: the joint is passively extended or flexed and the subject must report the perceived direction. In a conventional matching test, the subject actively moves the testing joint to match the reference joint on the opposite side of the body; the closeness of the match is thought to reflect static position sense.

However, these and other available clinical tests are subjective, poorly standardized, and too coarse to detect subtle changes. In addition, these tests do not control for the influence of muscle contraction history on proprioceptors (spindles) in the muscle (muscle thixotropy), which can bias proprioceptive measurements; and they typically require active or passive movement of the patient, creating a confound for patients with pain, spasticity, or motor deficits.

For example, a patient with pain may tense up with movement, providing extra stimulation to spindles and leading to over-estimation of proprioceptive acuity. The patient may have less pain on a return visit, yielding a more accurate proprioceptive estimate, but erroneously indicating a decrease in acuity since the first visit.

An additional limitation of current clinical tests is that proprioceptive sensitivity and bias are not readily distinguished. If a series of numerical measurements of proprioception is made, the spread of the subject's errors reflects the inverse of his proprioceptive sensitivity. If the mean of the errors is offset from true position, this offset represents a bias in perception. Sensitivity and bias are independent; in other words, proprioception can be very sensitive, but highly biased.

Perceptual sensitivity is thought to be represented in the brain in a Bayesian fashion, but sensory bias is less understood. Some clinical populations may have a deficit in proprioceptive sensitivity while may others have difficulties because their proprioception is biased.

A need therefore exists to develop a test that incorporates both sensitivity and bias, making it possible to tailor rehabilitation to the specific proprioceptive deficit. Although clinical tests of static position sense, such as matching, involve a movement before each trial, this need not be the case. Activity in a population of muscle spindle afferents does not stop when we stop moving. Background spindle activity continues, which, along with joint receptors and skin stretch input, the brain integrates into a body map to create a perception of position: static position sense.

Static position and movement senses are both critical for accurate movement. For example, to correctly plan a reach, the brain needs an accurate estimate of the hand's starting position. To monitor the movement in progress and make any needed corrections, the brain needs a good sense of movement. These sub-modalities share a common neural apparatus, including primarily spindles at non-extreme joint angles, spinal pathway, and processing in the somatosensory cortices and cerebellum. Static position sense may arise from summation of background activity in spindles, while movement sense may arise from changes in spindle activity that occur in proportion to changes in muscle length.

Without being limited to any theory, it is believed that position and movement information are simultaneously processed in the same neural networks. Thus, a disease or injury that impairs one sense is likely to impair the other. From a clinical standpoint, because of the limitations of tests involving movement, a movement-free clinical test of static position sense may have substantial advantages. A need therefore exists to develop a test that would be standardized and objective, reliable, simple to apply, portable, inexpensive, and easy for patients to complete.

SUMMARY

In some aspects of this disclosure, stands for measuring proprioception may include a hand layer comprising one or more vertically offset portions configured to ensure proper placement of a patient's hand in a predetermined position, a top cover coupled to the hand layer, wherein the top cover is designed to obscure the patient's view of the patient's hand, and a support element coupled to the hand layer and configured to support the hand layer at a predetermined angle.

In various aspects of this disclosure, methods of measuring a patient's proprioception may include placing a patient's hand on an angled stand beneath a display screen with a portion of the patient's hand at a predetermined angle, instructing a patient to apply pressure with the portion of the patient's hand that is at the predetermined angle, displaying, by the display screen, a test position of the portion of the patient's hand, and receiving, from the patient, an indication of a positional relationship between an actual position of the portion of the patient's hand and the test position on the display screen.

BRIEF DESCRIPTION OF THE DRAWINGS

The above mentioned and other features and objects of this disclosure, and the manner of attaining them, will become more apparent and the disclosure itself will be better understood by reference to the following description of exemplary embodiments of the disclosure taken in conjunction with the accompanying drawings, wherein:

FIGS. 12A-C illustrate group data on inter-rater reliability;

FIG. 17 is a table containing data from 12 individuals who had experienced ischemic or hemorrhagic stroke at least 6 months prior to collection.

Figure 1:
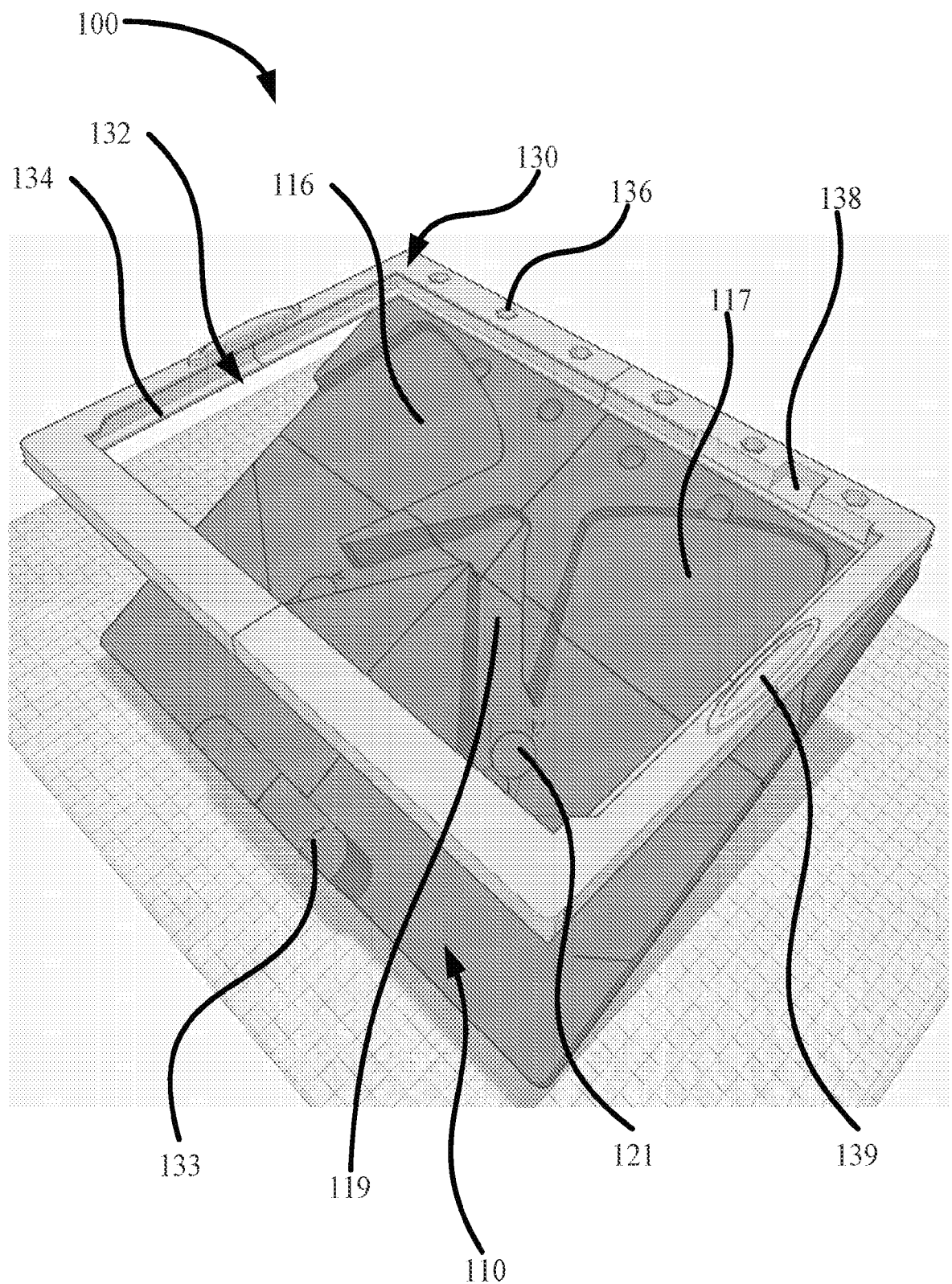
FIG. 1 is a perspective view of a stand for measuring proprioception according to various aspects of the present disclosure.

Corresponding reference characters indicate corresponding parts throughout the several views. Although the drawings represent embodiments or aspects of the present disclosure, the drawings are not necessarily to scale and certain features may be exaggerated in order to better illustrate and explain the present disclosure. The exemplifications set out herein illustrate exemplary aspects of the disclosure, in various forms, and such exemplifications are not to be construed as limiting the scope of the disclosure in any manner.

DETAILED DESCRIPTION

The aspects disclosed below are not intended to be exhaustive or limit the disclosure to the precise form disclosed in the following detailed description. Rather, the aspects are chosen and described so that others skilled in the art may utilize its teachings.

As used herein, the modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range "from about 2 to about 4" also discloses the range "from 2 to 4."

FIG. 1 shows a perspective view of a stand for measuring proprioception according to various aspects. Stand 100 may comprise a hand layer 110 comprising one or more raised portions configured to ensure proper placement of a patient's hand in a predetermined position. Stand 100 may also comprise a top cover 130 in mechanical communication or coupled with hand layer 110, wherein the top cover is designed to obscure a patient's view of the patient's hand. By coupling the top cover to the hand layer, the position of the display 131 held by the top cover 130 may be correctly aligned with the rest of the stand and the hand of the patient.

Figure 5:
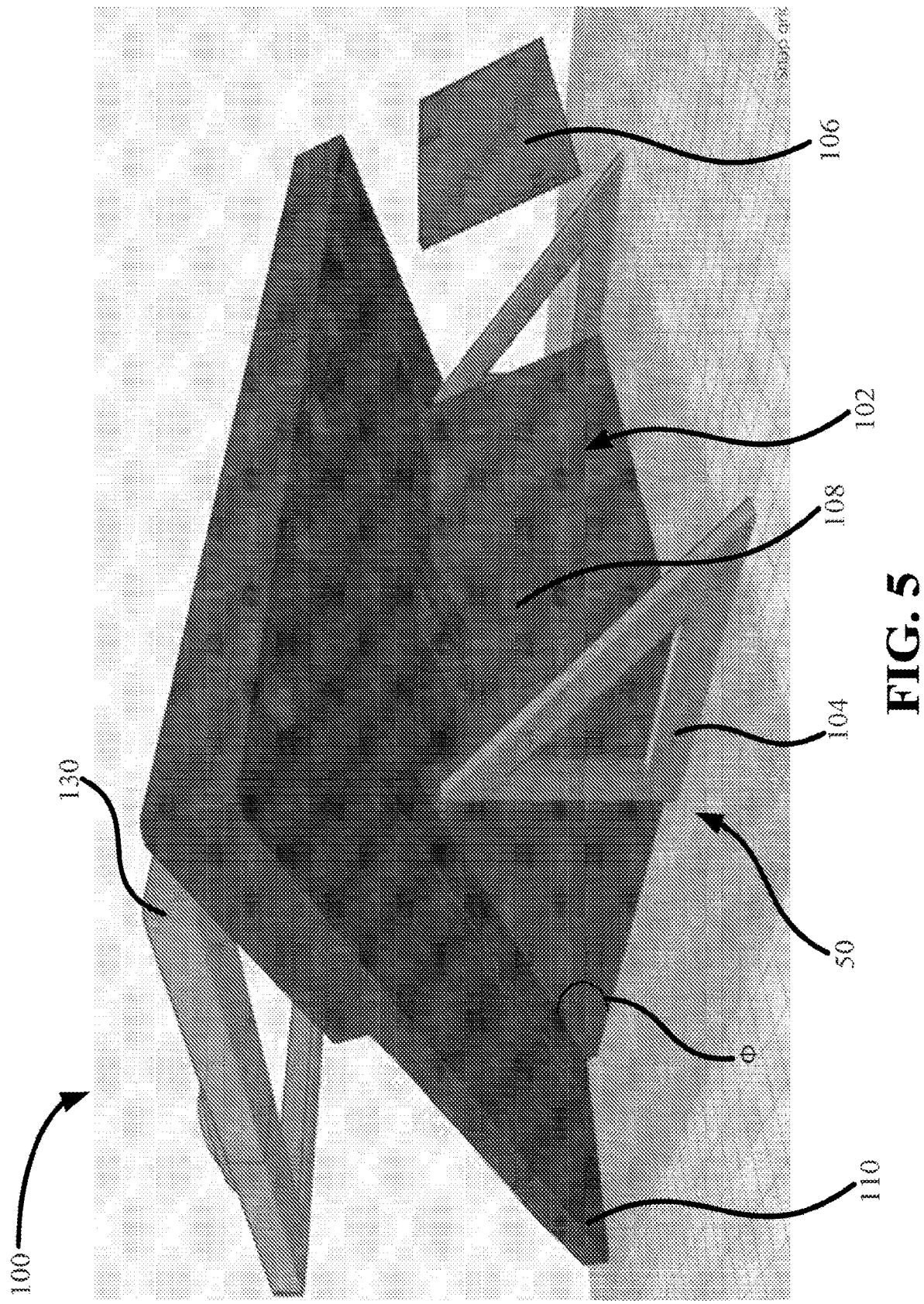
FIG. 5 is an expanded perspective view of the back of a stand for measuring proprioception.
Figure 6:
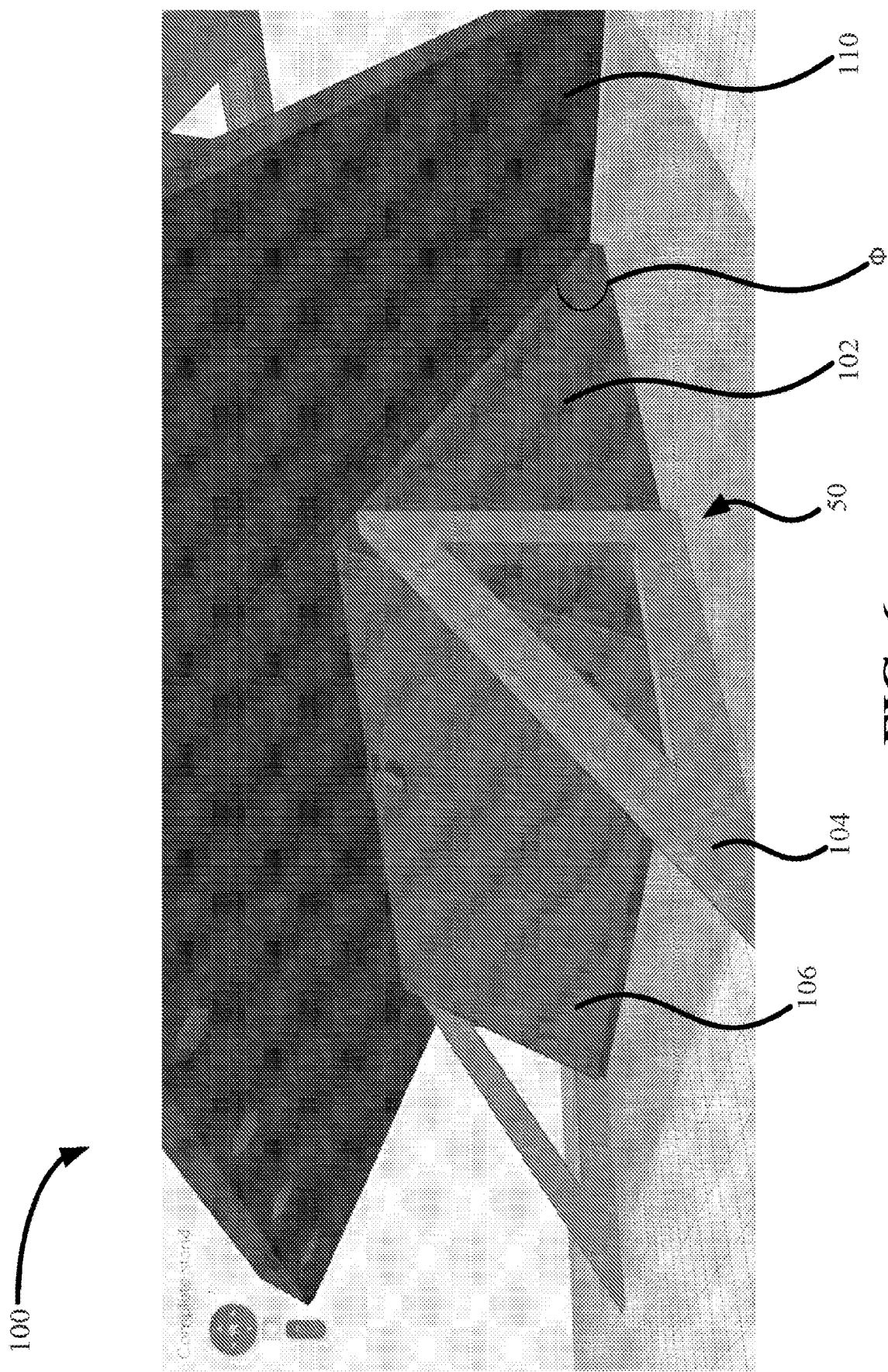
FIG. 6 is an perspective view of the back of a stand for measuring proprioception.

With temporary reference to FIGS. 5 and 6, a support element 50 may be coupled to the hand layer 110 and configured to support the hand layer at a predetermined angle Φ. The predetermined angle Φ is not particularly limited and may be measured as the angle between a sagittal plane of a patient and a medial of the patient. Predetermined angle Φ may be between about 10 degrees to about 45 degrees, between about 20 degrees to about 30 degrees, or about 25 degrees according to various aspects.

Figure 7A:
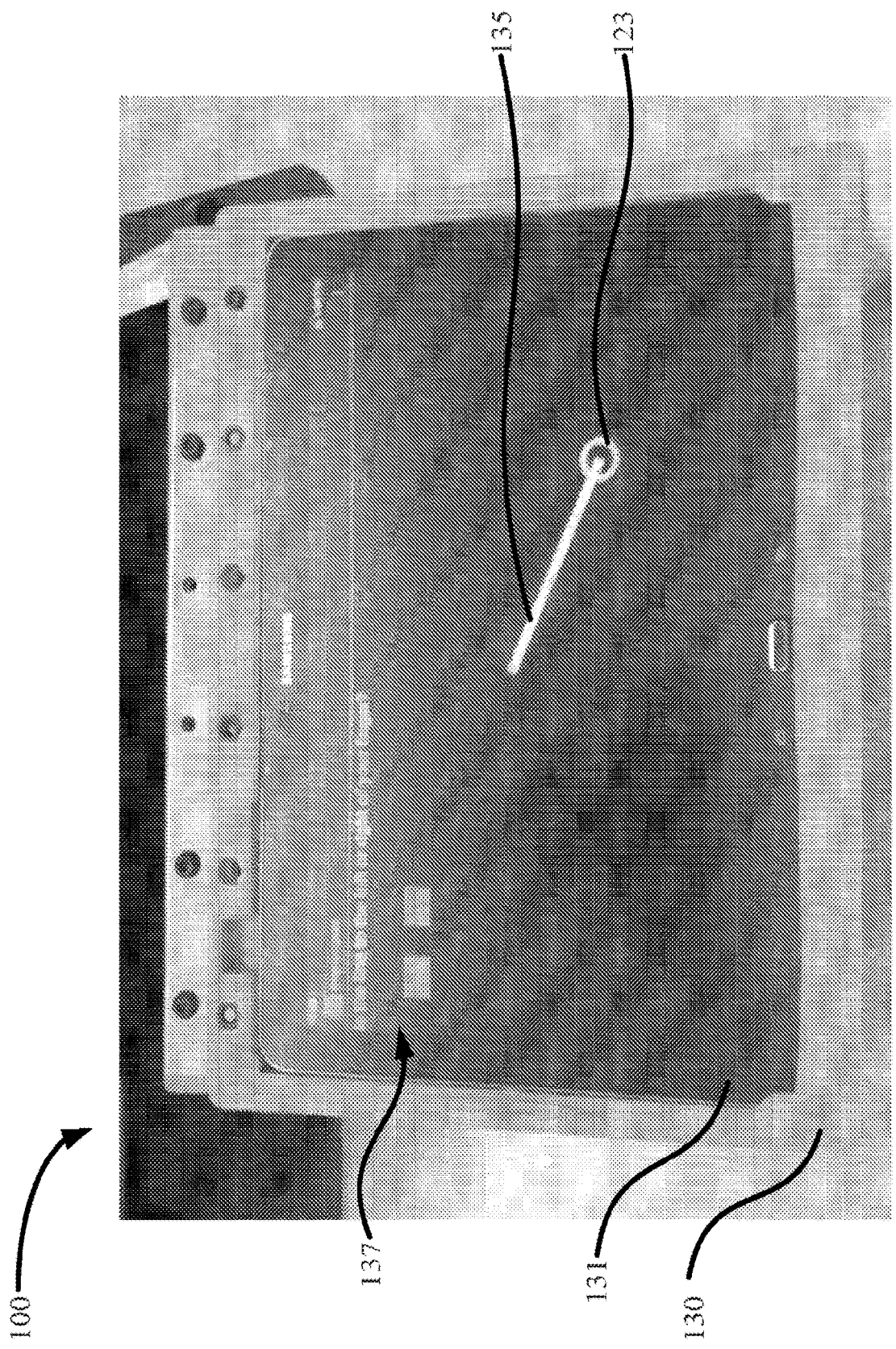
FIG. 7A illustrates a stand with a display according to various aspects.

With continued reference to FIG. 1, the top cover 130 may also be configured to hold a display (display shown as display 131 in FIG. 7A). Thus, top cover 130 may comprise aperture 132 configured to hold the display 131, for example, with top cover lip 134. In various embodiments, top cover 130 may be moveably coupled (e.g., hinged) to hand layer 110. For example, bolts or screws in openings 136 may help secure hinges (not shown) to top cover 130 and hand layer openings 135 (shown in FIG. 2) may be used to secure hinges to hand layer 110. In various aspects, top cover 130 may be hinged to allow for the raising and lowering of the display 131 and/or the top cover 130 over a patient's hand. Top cover grips 139 may facilitate in the raising and lowering of top cover 130, while slot 138 may facilitate placement and/or removal of the display 131. Thus, in some aspects, the top cover 130 may be configured to hold a display.

Hand layer 110 may include one or more vertically offset portions configured to ensure proper placement of a patient's hand in a predetermined position. As used herein, the term vertically offset may include a raised or a depressed portion. For example, hand layer 110 includes a left hand depression 116 and right hand depression 117 for placement of the middle finger, ring finger, and the little finger. Hand layer 110 may also comprise top layer support 133, which may support the top cover when in place. Hand layer 110 may also include right index finger in depression 119 (shown in FIGS. 1 and 2) and left index finger depression 118 (shown in FIG. 2). In some aspects, the hand layer 110 may comprise a tactile portion, such as left tactile portion 120 (FIG. 2) and right tactile portion 121, configured to engage a predetermined portion of the patient's hand. In some aspects, this may help to ensure proper initial placement of the patient's hand and may also help in allowing the patient to identify portions of the hand (e.g., the distal portion of the index finger) in relation to another portion of the hand (e.g., in relation to the index knuckle).

Figure 2:
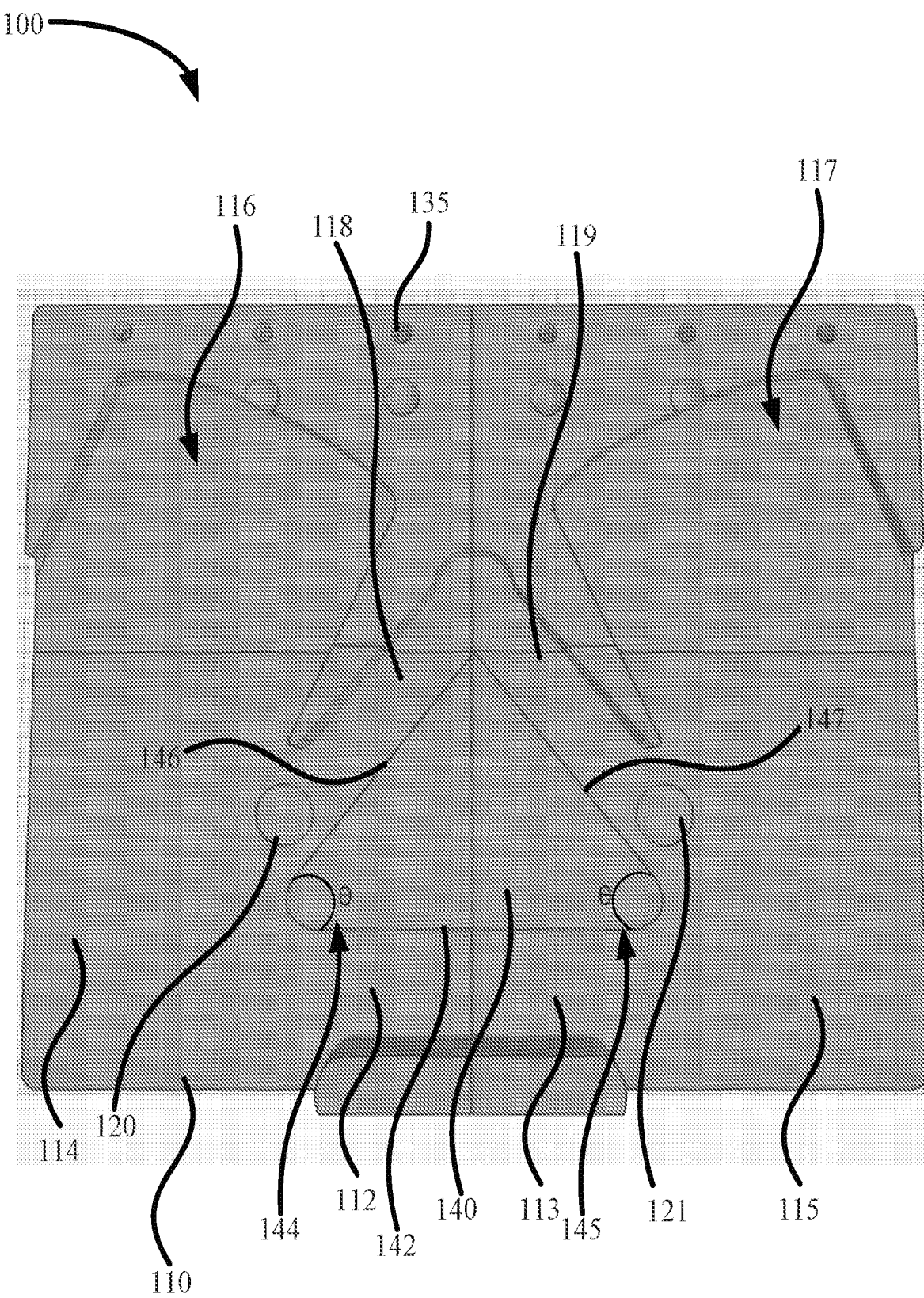
FIG. 2 is a perspective view of the hand layer according to various aspects.

As shown in FIG. 2, thumb placement can occur in right thumb depression 113 and left thumb depression 112. Raised portion 140 may separate the index fingers from the thumb of a patient. Raised portion 140 may comprise a left angle θ 144 (the angle between left lower index finger wall 146 and upper thumb wall 142) and a right angle θ 145 (the angle between right lower index finger wall 147 and upper thumb wall 142). The left angle θ 144 and the right angle θ 145 are not particularly limited and may be between about 70 degrees and about 35 degrees, between about 65 degrees and about 45 degrees, between about 60 degrees and about 50 degrees, or about 50 degrees according to various aspects.

In various embodiments, the predetermined position may be measured from an angle that is orthogonal to a sagittal plane of a patient. Thus, in various aspects, the predetermined position positions an index finger of the patient's hand at an angle between about 50 degrees and about 60 degrees from an axis orthogonal to a sagittal plane of the patient, or at an angle of about 55 degrees from an axis orthogonal to a sagittal plane of the patient.

Figure 3:
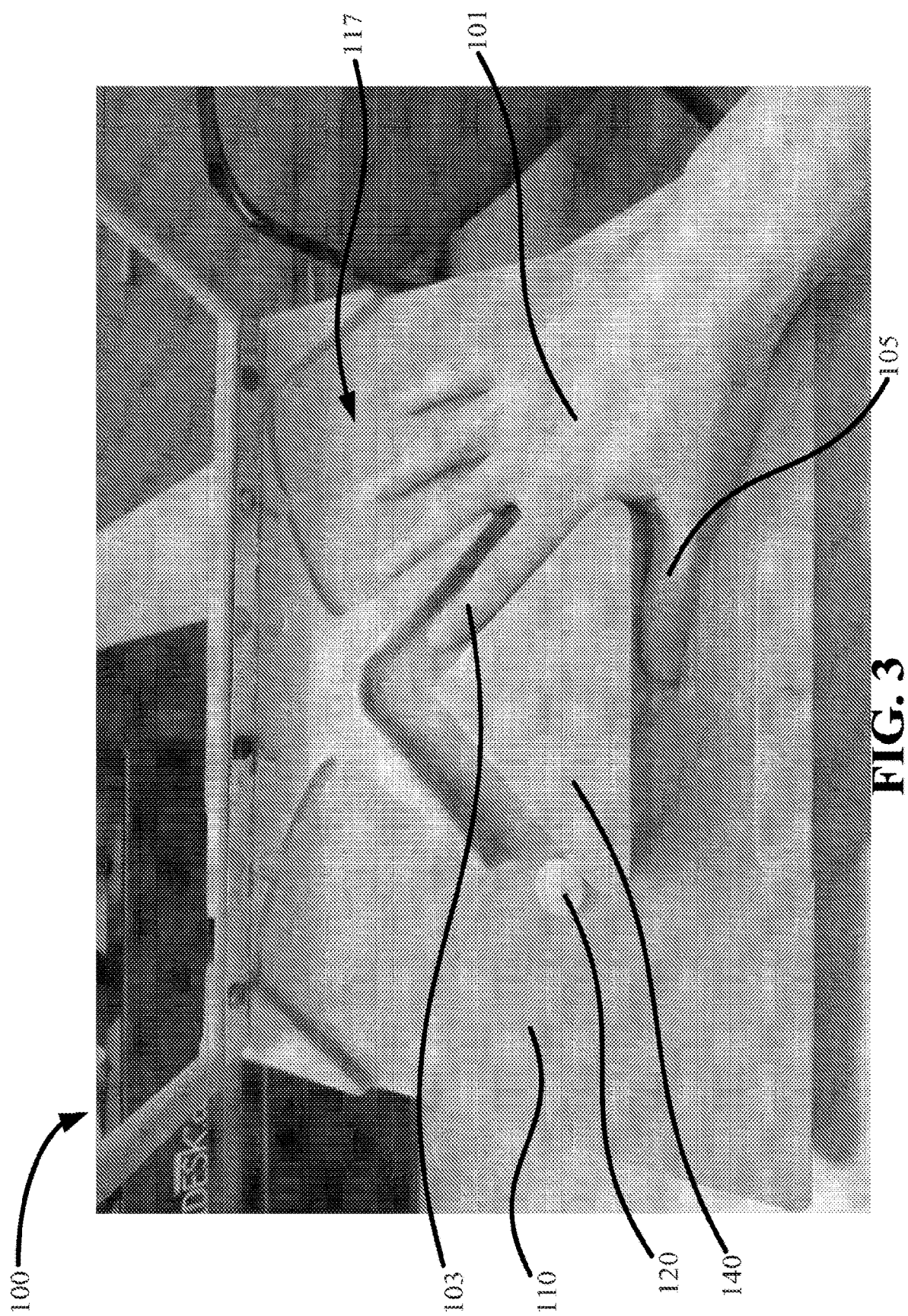
FIG. 3 is a photo showing hand placement on the hand layer according to various aspects.

Left wrist rest 114 and right wrist rest 115 may be used to allow the patient to rest the entire hand and wrist on hand layer 110. For example, with respect to FIG. 3, placement of patient's hand 101 is shown. As can be seen in FIG. 3, patient's right index finger 103 is separated from patient's thumb 105 by raised portion 140, with the middle finger, index finger, and small finger resting on right hand depression 117.

Figure 4:
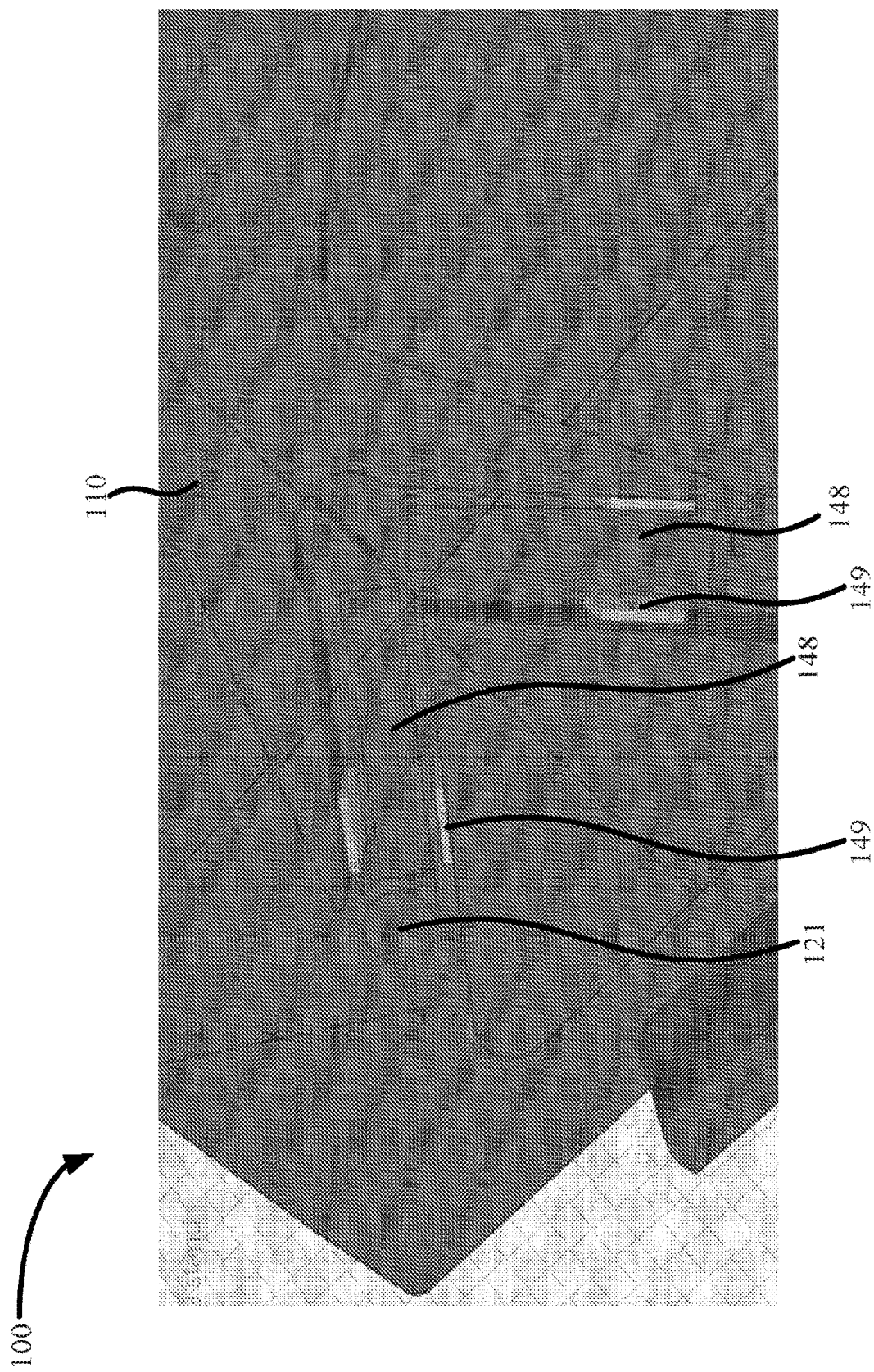
FIG. 4 is a perspective view showing pressure sensors integrated with the hand layer according to various aspects.

In various aspects, various stands may include a pressure sensor operationally coupled to the hand layer. For example, FIG. 4 illustrates a hand layer 110 with a pressure sensor 148 operationally coupled to the hand layer 110. In various aspects, the pressure sensor 148 may be integrated with the hand layer 110. In various aspects, the pressure sensor may be configured to determine movement of the patient's hand. Additionally, finger clamps 149 may be used to help guide parts of a patient's hand and/or may also help to avoid movement of the patient's hand by the patient.

With reference to FIGS. 5 and 6, a support element 50 according to various embodiments is shown. FIG. 5 illustrates an expanded view of support 50 coupled to the hand layer 110 and configured to support the hand layer 110 at a predetermined angle Φ. The predetermined angle Φ is not particularly limited and may be measured from a sagittal plane of a patient and a medial of the patient. In various aspects, the predetermined angle Φ may be between about 10 degrees to about 45 degrees, between about 20 degrees to about 30 degrees or about 25 degrees.

Support element 50 may also comprise legs and crossbar element 104. In various embodiments, support element 50 may also comprise electrical unit housing 102 that may comprise slot 108 configured to receive an electrical unit (not shown), such as a pressure sensor, which may include a pressure sensor, a processor, and memory. Back cover 106 may be configured to completely encase the electrical unit. In various aspects, the processor may be in electrical communication with the pressure sensor and a non-transitory computer readable storage medium bearing instructions for automating determination of muscle thixotropy.

Various processors include any suitable processing device or devices operative to execute the software/firmware stored in memory. For example, the processor may include one or more programmable processors (e.g., central processing unit (CPU) devices), application-specific integrated circuits (ASICs), field-programmable gate arrays (FPGAs), digital signal processors (DSPs), hardwired logic, or combinations thereof.

One of ordinary skill in the art will realize that the embodiments provided can be implemented in hardware, software, firmware, and/or a combination thereof. Programming code according to the embodiments can be implemented in any viable programming language such as C, C++, HTML, XTML, JAVA or any other viable high-level programming language, or a combination of a high-level programming language and a lower level programming language.

Figure 7B:
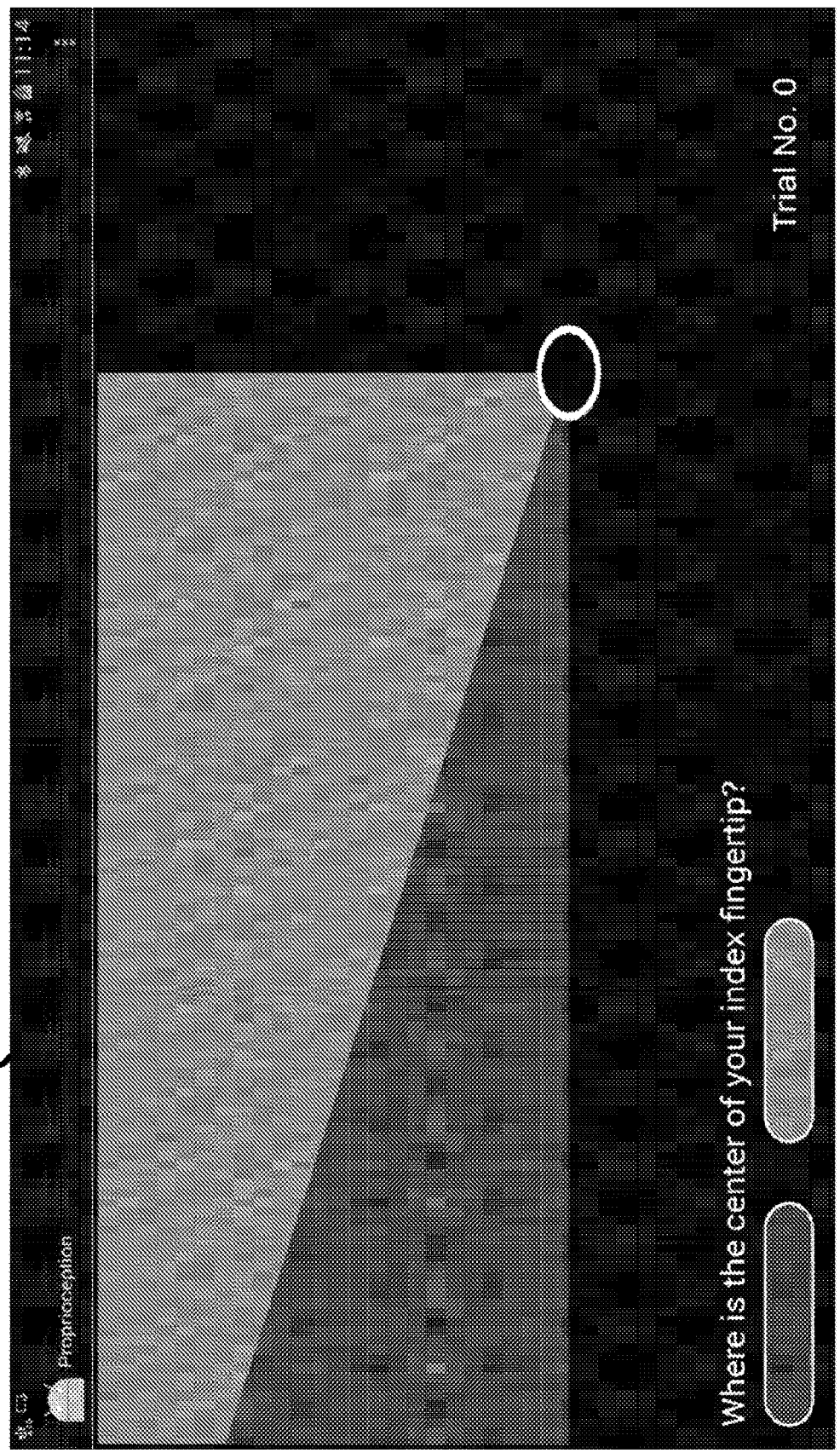
FIG. 7B illustrates a display according to an aspect of the disclosure.
Figure 8:
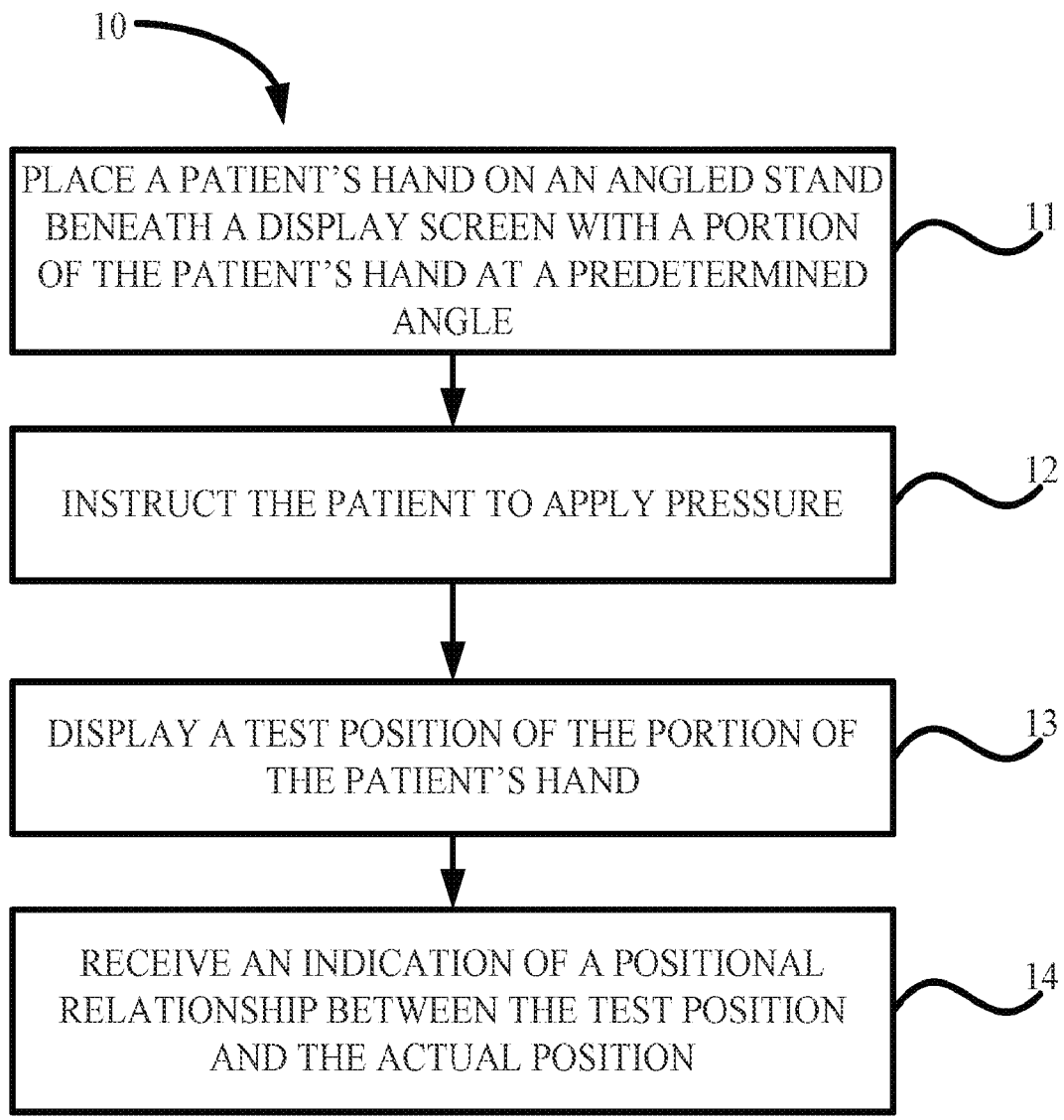
FIG. 8 illustrates a flow diagram of a method of proprioception.

Method 10 of FIG. 8 includes placing a patient's hand on an angled stand beneath a display screen with a portion of the patient's hand at a predetermined angle (step 11) and instructing the patient to apply pressure (e.g., briefly apply pressure) with the portion of the patient's hand that is at the predetermined angle (step 12). In various aspects, method 10 may also include displaying, by the display screen, a test position of the portion of the patient's hand (step 13) and receiving, from the patient, an indication of a positional relationship between the actual position of the portion of the patient's hand and the test position on the display screen (step 14), as shown in FIGS. 7A and 7B and as further described below.

FIG. 7A illustrates the stand 100 being used in an exemplary method for measuring a patient's proprioception, such as the method exemplified in FIG. 8. In FIG. 7A, display 131 housed in top cover 130 contains an indicator showing the portion of the patient's hand corresponding to right tactile portion 121 (shown as 123) and a test position of the portion of the patients hand 135. In the aspect shown in FIG. 7, the patient is able to give an indication of a positional relationship between the actual position of the portion of the patient's hand and the test position on the display screen (step 14) through the responding to questions 137. For example, in FIG. 7A the question is exemplified as "Is the line to the left or right of your finger."

In one aspect exemplified in FIG. 7B, the question on display 131 may inquire where the patient feels the center of a digit of their hand (e.g., the index finger) is located. By altering the display to inquire about varying test positions, the proprioception of the patient may be objectively measured.

In some aspects, methods may also include repeating one or more of the aforementioned steps, such as repeating the displaying the test position indicating the test position, but varying the display for each question. Thus, in various aspects, this may be done repeatedly with a plurality of test positions. In some aspects, the repeating the displaying of the test position may repeated with an adaptive staircase method as further described below.

For example, an initial difference between the test position and the predetermined angle is about 30 degrees and the subsequent differences between the test position and the predetermined angle may decrease using an adaptive staircase method. For example, a subsequent difference between the test position and the predetermined angle may be about 10 degrees.

The information regarding a patient's proprioception is not limited and may include (i) determining a bias by either fitting a function (e.g., a sigmoidal function) to the data or averaging a plurality reversal angles with an adaptive staircase method and/or may include (ii) determining a proprioception sensitivity by fitting a function to the data or determining a standard deviation of a plurality of reversal angles. Methods may also include measuring and/or controlling the pressure of the portion of the patient's hand on the angled stand.

Test Data

Forty-eight (48) healthy right-handed adults (aged 18-82, 16 male) participated in the study. All three tests were performed in each session, with the order randomized. Study procedures were approved by the Indiana University Institutional Review Board. Subjects gave written informed consent and completed questionnaires about general health and activities: years playing a sport or musical instrument and average hours played per week. For all three techniques, subjects were seated in front of a table, with the apparatus on the table positioned centrally. The elbow was bent about 90° and slightly in front of the body, with the forearm resting on the table. The hand was pronated on the 25° apparatus, about 20 cm in front of the body and centered with the trunk midline. The index finger was positioned at 55° to the subject's trunk and the other fingers were slightly spread.

Measurement Procedures

Adaptive Staircase

The blindfolded subject's right hand was positioned on an angled stand, with the MP joint of the second finger on a tactile marker and the index finger pointing along a 55° line. The experimenter was aided by the outline of a hand drawn on the stand. The subject was instructed to press firmly against the experimenter's finger and then relax to ensure a consistent history of muscle contraction across subjects (a control for muscle thixotropy). Finally, a tablet-style computer screen (13×9 inches, 8 mm thick) was placed over the subject's hand. The blindfold was removed and the subject instructed not to move the right hand further.

Subjects viewed the display of a custom MATLAB program, a white line on a dark background. The line began directly over the tested joint (represented by a circle) and extended the length of the finger. Subjects were asked to report whether the end of the line was located to the right or left of their index fingertip. Six staircases were completed for each application of this method. The first two staircases began 30° to the left and right of the true finger position (55°). If the subject's response was correct (e.g. "left" when the white line was 30° to the left of the finger), the line moved 10° towards true finger position and the subject was again asked to report their perception. As the line approached true finger position, the choice of right or left became less obvious; eventually the subject felt the white line had overshot their finger and changed their reported direction.

Whenever reported direction changed, the line reversed direction and step size decreased by half to yield more measurements near the subject's perceptual boundary (the angle at which the subject is equally likely to report "left" or "right"). The first two staircases terminated when the subject had reversed direction four times. To increase the number of angles sampled near the subject's actual perceptual boundary, a rough estimate of the boundary (mean of the last four angles tested in each staircase) and sensitivity (0.75 of the range of these 8 angles) in the subject's perception was then calculated online. The subsequent four staircases were centered on the subject's rough perceptual boundary, rather than true finger position, and began to the left or right (two each) at an angular distance equal to the subject's rough sensitivity. Initial step size for these staircases was 5°, and each staircase terminated when the subject had reversed direction four times. The mean number of proprioceptive estimates subjects made in the six staircases was 58±12. Subjects were given no feedback on their performance.

For each angle tested during the six staircases, the program calculated the number of responses obtained and the proportion that were "right" rather than "left." This individual dataset was fit with a logistic regression model, chosen both because the data come from a binomial distribution and because this limits the predicted proportions to [0 1]. The 50% point of the fitted function was interpreted as the subject's perceptual boundary, equivalent to the bias in the proprioceptive estimate of that joint's position. The angular difference between the 25% and 75% points of the function was interpreted as a representation of the sensitivity in the subject's proprioceptive estimate, with a smaller value reflecting greater sensitivity. Across individuals, the boundary and sensitivity obtained from the fitted function were nearly identical to those obtained from the mean and standard deviation of the angles at which the subject reversed direction (correlation $r>0.98$, $p<10\text{-}30$ for boundary and $r>0.92$, $p<10\text{-}20$ for sensitivity), suggesting the function fit was good. To assess whether a shortened version of this test would compare favorably with the other methods, this data was re-analyzed using only the first two staircases.

Matching

To maximize consistency across subjects and experimenters, a matching task that is less subjective than what might be done in a clinical setting was devised, but still simple enough to be used clinically. Blindfolded subjects placed both hands on an inclined custom angle board: the right hand (reference hand) on the right panel and the left (indicator hand) on the left panel. The experimenter placed the hands such that the MP joint of each index finger was on a tactile marker where the lines intersect. Both panels had the outline of a hand drawn to aid the experimenter with positioning, plus a thick line at ±55° to indicate mirrored positions. Lines of different colors were drawn on the left panel in steps of 10, 5, 2.5, and 1.25°. After controlling for muscle thixotropy, the experimenter moved each index finger in turn and then placed the right index finger along the 55° line. Participants were then instructed to move the left index finger to mirror the right. The left finger's final position was recorded in terms of angular deviation from a perfectly mirrored position (0°). This trial was repeated ten times, with the experimenter moving and placing both index fingers before each trial to discourage subjects from using remembered positions. The subject's proprioceptive bias and sensitivity were calculated as the mean and SD of the ten errors.

Passive Movement Direction Discrimination Threshold (PMDD).

Rather than test the clinically-used PMDD, a less-subjective version that could still be used clinically was devised. PMDD was tested on the left panel of the inclined angle board. Experimenters placed the blindfolded subject's right hand so that the MP joint of the index finger was on the tactile marker where the lines intersect. To reduce extraneous sensations during passive movement, the index finger was taped to a smooth stick 1.5×0.75×10 cm. After controlling for muscle thixotropy, the experimenter moved the finger 5° left or right. Subjects were asked to report perceived movement direction, then the finger was moved back to neutral. Experimenters touched only the stick during movements, to avoid giving the subject pressure cues. To control for movement speed, experimenters counted two seconds between each 1.25° line on the board, equivalent to 0.625°/s. For each tested angular magnitude, the subject experienced six movements: 3 to the left and 3 to the right, in randomized order. If the subject made a mistake at 5 degrees, angular magnitude was increased to 10°, and subsequently to 15° if mistakes were made at 10°. If the subject did not make mistakes at 5 degrees, angular magnitude was decreased to 2.5°, and then to 1.25° if no mistakes were made at 2.5°. The PMDD threshold was recorded as the smallest angle at which the subject did not make mistakes. The largest angular magnitude tested, due to biomechanical constraints, was 15°. The smallest angle tested, due to constraints of the angle board, was 1.25°.

Analysis

Test-retest reliability was calculated with intraclass correlation coefficients for each of 5 dependent variables (adaptive staircase boundary and sensitivity; matching mean and SD; PMDD threshold), comparing Session 1 to Session 2. For Inter-rater reliability, intraclass correlation coefficients for each of the 5 dependent variables, comparing Rater 1 (YL) to Rater 2 (BS) was calculated.

For construct validity a stepwise method was used to perform a multiple regression of each of the five dependent variables on three predictive terms: age, sport years×hours per week, music years×hours per week. Correlations between each pair of tests was calculated for an adaptive staircase boundary vs. PMDD threshold, adaptive staircase boundary vs. matching mean, matching mean vs. PMDD threshold, as well as equivalent pairs involving measures of sensitivity.

Results

Twenty (20) of the forty-eight (48) subjects completed two experimental sessions each and were included in the test-retest analysis. The sessions were on average 14.9±10.7 days apart. The remaining twenty-eight (28) subjects completed one session each. For the eleven subjects (age 20-73, 3 male) included in the inter-rater analysis, measurements were performed twice in a single session by two different experimenters. At the end of each session, subjects were asked to rate their quality of sleep, fatigue from the session, and attention during the session on a scale from one to ten, with ten being the most. Subjects reported an average (±SD) of 7.5±1.3, 3.3±2.2, and 8.2±1.1, respectively.

Test-Retest Reliability

Figure 9A:
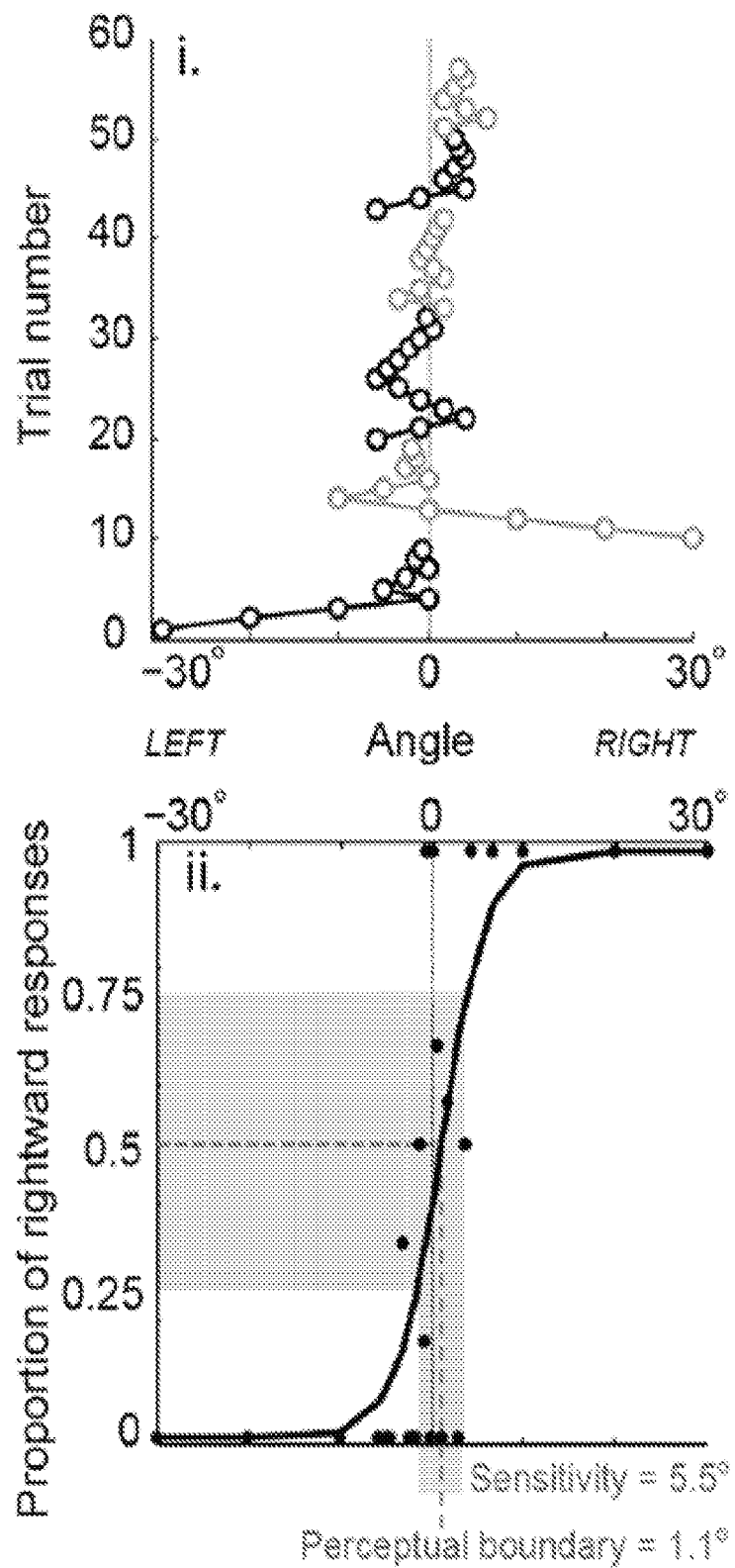
FIGS. 9A and 9B illustrate adaptive staircase performance of a younger subject in two sessions conducted ten days apart.
Figure 9B:
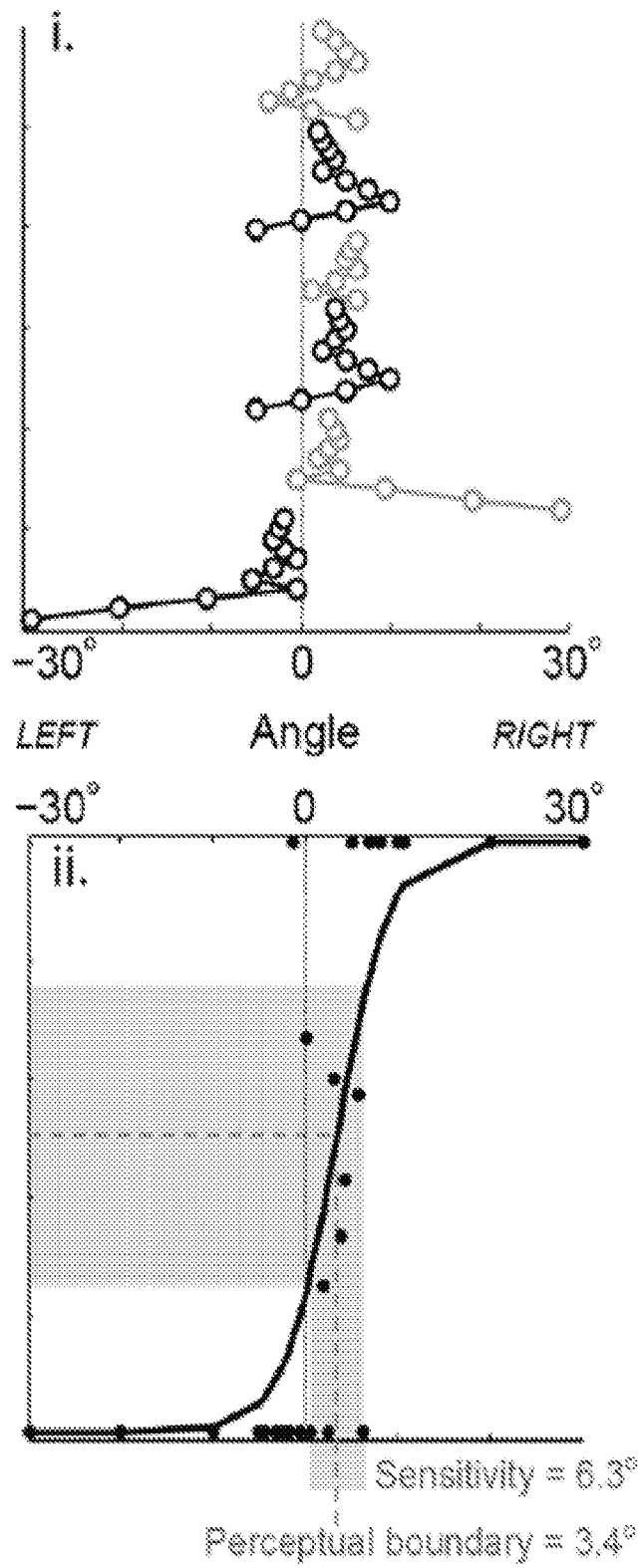
Figure 10A:
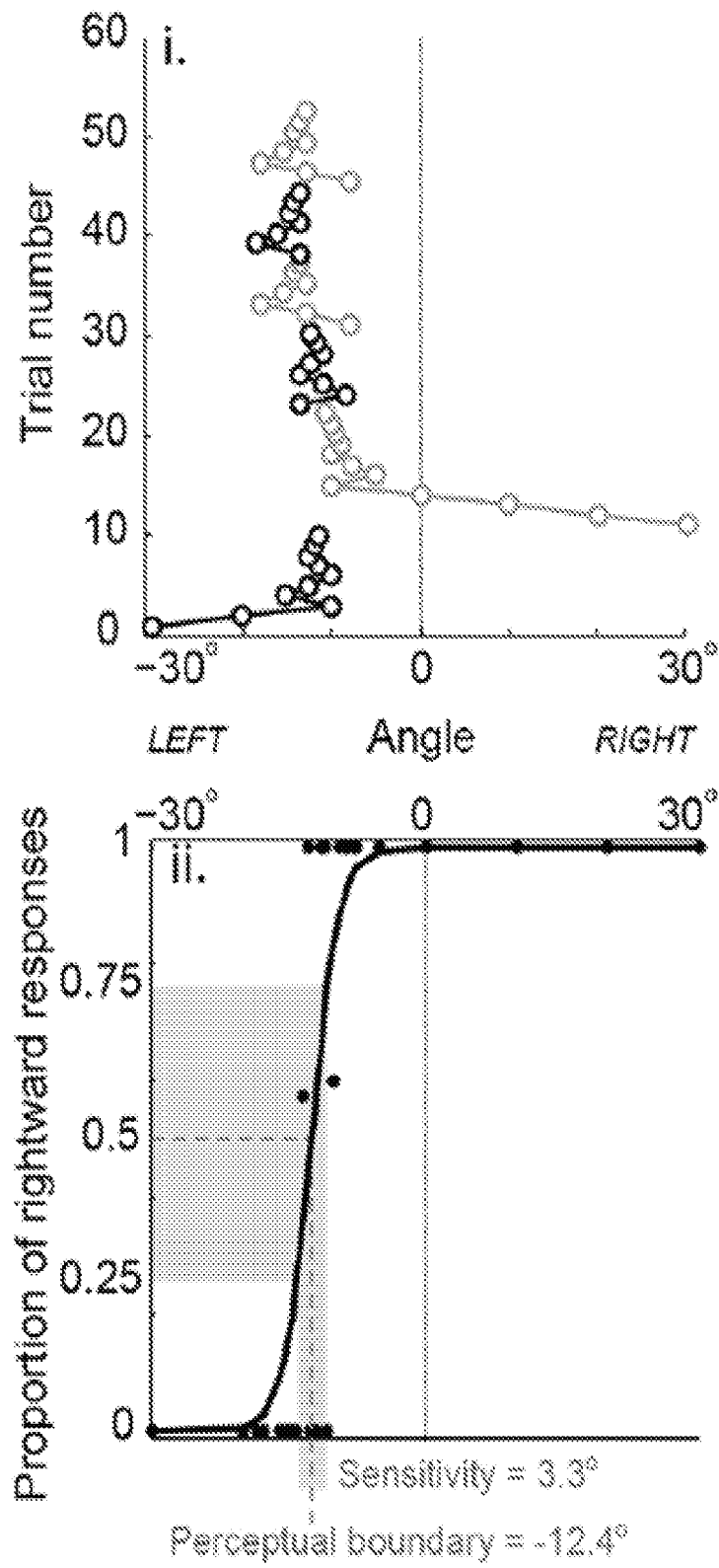
FIGS. 10A and 10B illustrate adaptive staircase performance of a subject aged 56 in two sessions conducted ten days apart.
Figure 10B:
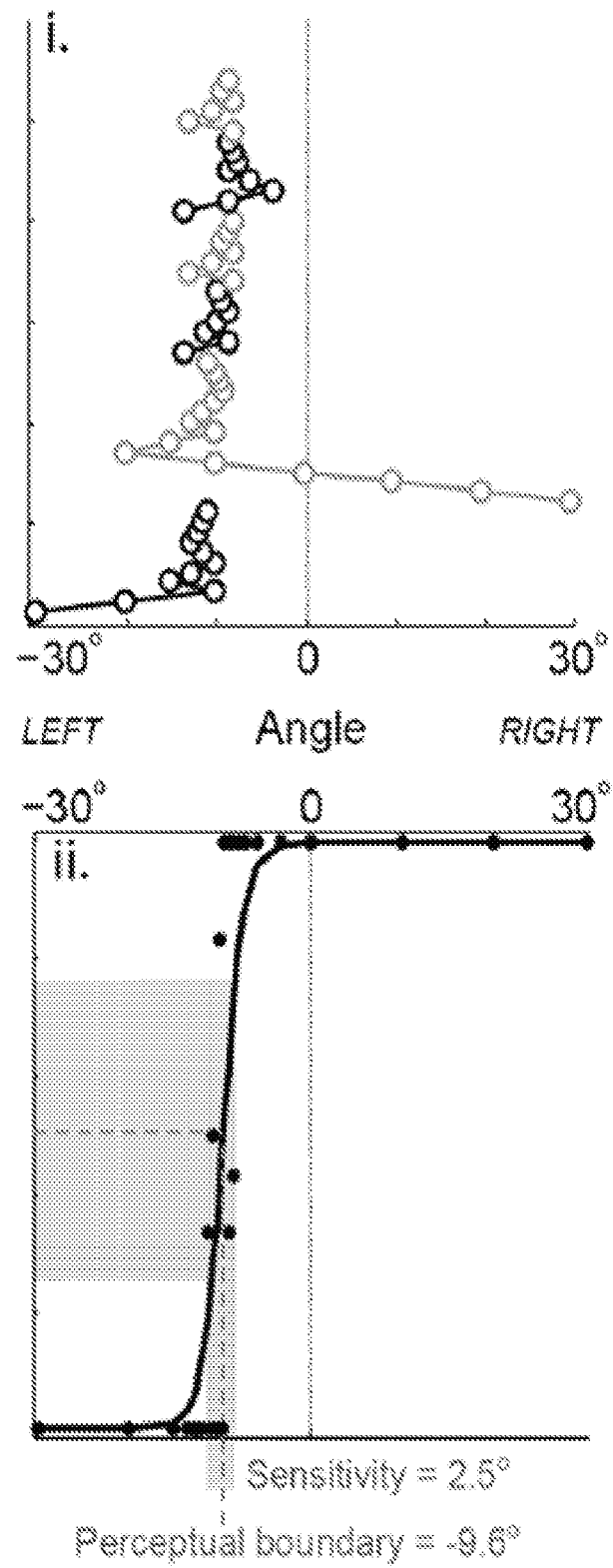

Perceptual boundary (proprioceptive bias) as measured by the adaptive staircase technique showed the most stability. This was evident across the age range of subjects. Young subjects typically showed very small proprioceptive biases (e.g., FIGS. 9A-C), while older subjects often showed larger proprioceptive biases (e.g., FIGS. 10A-C). The spread of proprioceptive estimates (sensitivity) with the adaptive staircase method also appeared consistent across sessions, but no difference between older and younger adults was evident.

Figures 11A, 11B, 11C:
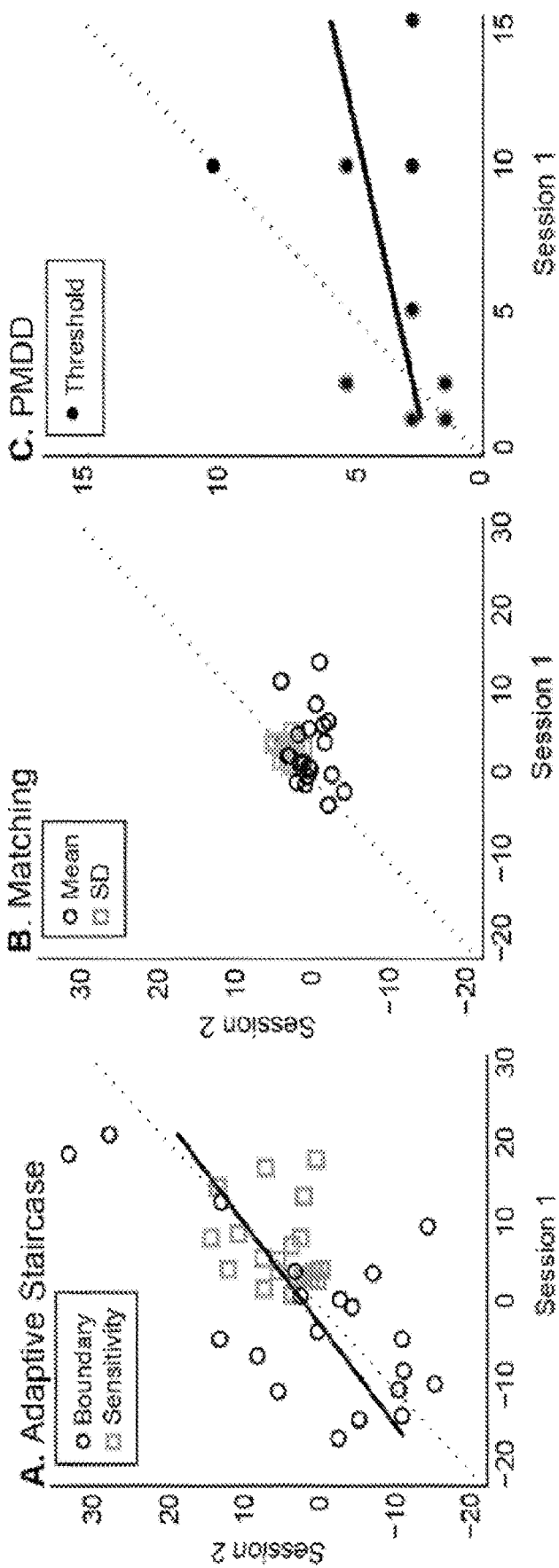
FIGS. 11A-11C illustrate group data on test-retest reliability.

This pattern was observed in the group data as well. Proprioceptive bias—as assessed with the adaptive staircase technique—yielded the strongest test-retest reliability, whether the full 6 staircases were analyzed (ICC R=0.62, p=0.001; shown in FIG. 11A) or a short version including only the first two staircases (ICC R=0.59, p=0.002). One subject is an outlier according to quartile analysis, but as ICC is still significant after exclusion (ICC R=0.52, p=0.008), this subject did not appear to drive the relationship. Proprioceptive sensitivity, however, was not as stable (ICC R<0.22, p>0.17), which may be accounted for by the lack of spread in this population. The matching method appears the least stable (bias ICC R=−0.07, p>0.6; sensitivity ICC R=0.18, p>0.22; shown in FIG. 11B), with the PMDD method in between (ICC R=0.34, p=0.007; shown in FIG. 11C). The PMDD data also suggests a learning effect, with thresholds decreasing for nearly all subjects in their second session.

Inter-Rater Reliability

Adaptive staircase measurement of perceptual boundary also yielded the greatest inter-rater reliability (shown in FIG. 12A). This was the case for both the long (ICC R=0.86, p<0.001) and short (ICC R=0.76, p=0.0015) versions of the test. However, inter-rater reliability was poor for proprioceptive sensitivity with both versions (ICC R<0.20, p>0.13), again perhaps due to the small range of sensitivity in this healthy population. Matching showed the next highest inter-rater reliability for proprioceptive bias as assessed by the mean of 10 trials (ICC R=0.60, p=0.016), and the highest for proprioceptive sensitivity as assessed by the SD of 10 trials (ICC R=0.77, p=0.0012; shown in FIG. 12B). In contrast the PMDD measurement yielded weak inter-rater reliability (ICC R=0.40, p=0.089; shown in FIG. 12C). Clear differences between the raters are evident, with Rater 2 finding higher thresholds than Rater 1 (shown in FIG. 12C).

Figures 13A, 13B, 13C:
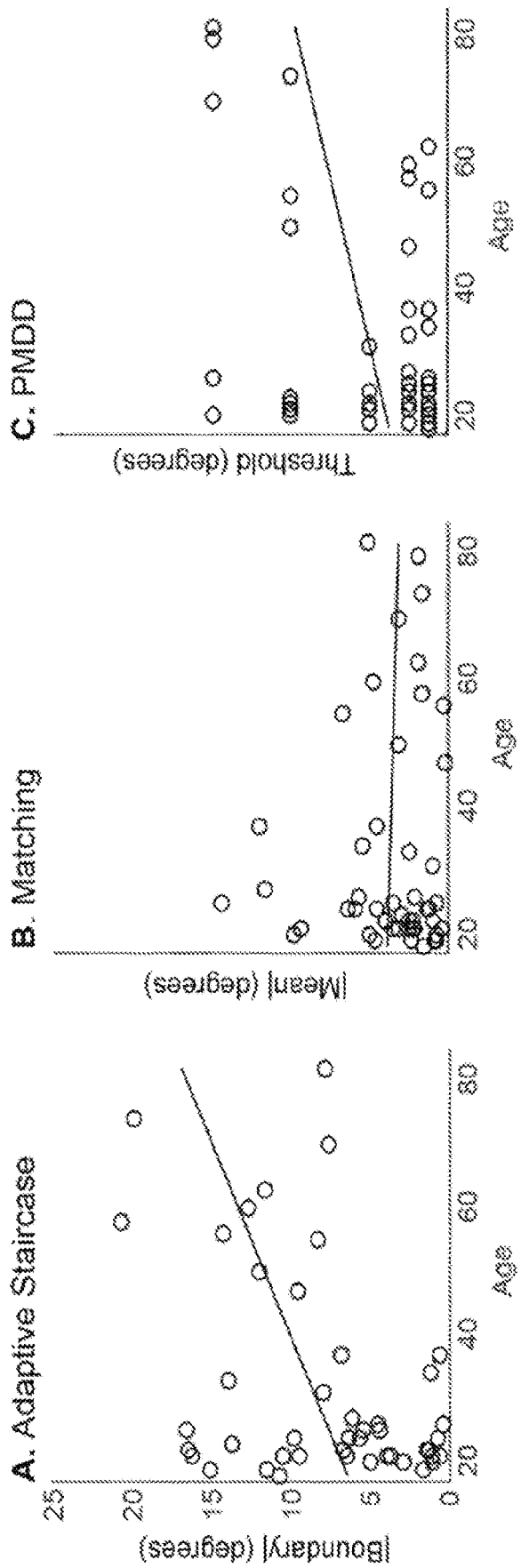
FIGS. 13A-C illustrates group data on construct validity.

Stepwise regression on age, sport years×hours per week, and music years×hours per week yielded only age as a significant predictive term for any of the three techniques. Age most strongly predicted proprioceptive bias as assessed by the adaptive staircase perceptual boundary (long method $R^2$=0.17, p=0.003; short method $R^2$=0.13, p=0.012). This is illustrated at the individual level by FIGS. 9A-C and 10A-C; older subjects tended to have larger proprioceptive biases than younger subjects (shown in FIG. 13A), a difference that was maintained across multiple sessions. No significant predictors were found for proprioceptive sensitivity with the adaptive staircase method. PMDD threshold was also predicted by age ($R^2$=0.13, p=0.011). However, no significant predictors were found for either mean or SD of the 10 estimates obtained in the matching method (shown in FIG. 13B). There was a tendency for adaptive staircase boundary to be correlated with PMDD threshold (R=0.21, p=0.081) and for adaptive staircase sensitivity to be correlated with matching SD (R=0.21, p=0.079), which may support the construct validity of the adaptive staircase method. There were no other significant or trend correlations across methods, using either proprioceptive bias or sensitivity measures (p's>0.1).

Various aspects of the novel techniques for measuring proprioception disclosed herein (adaptive staircase method) was compared with modified versions of two tests already used clinically (matching and PMDD). Substantial differences in test-retest reliability, inter-rater reliability, and construct validity were found. Proprioceptive bias assessed by adaptive staircase method was strongest in all three analyses. A shortened version (about twenty trials instead of about sixty) performed nearly as well in all areas, and better than matching or PMDD. The matching method may be the weakest of those tested, having statistically significant inter-rater reliability only. The PMDD trended toward test-retest and inter-rater reliability, although with noticeable biases between days and raters, and was significantly predicted by age, indicating good construct validity.

The adaptive staircase method is an application of psychophysical techniques to proprioception. As a scientific discipline, psychophysics investigates the connection between physical stimuli and subjective responses via the psychometric function. Responses are often obtained using a staircase procedure: the stimuli are presented in ascending or descending order of strength, with the subject choosing one of two options for each stimulus (two alternative forced choice), e.g. left or right. A series of staircases can then be used to create the psychometric function. This technique has historically been used to test visual perception, e.g. to assess the perception of color, brightness, and other properties.

Figures 14A, 14B:
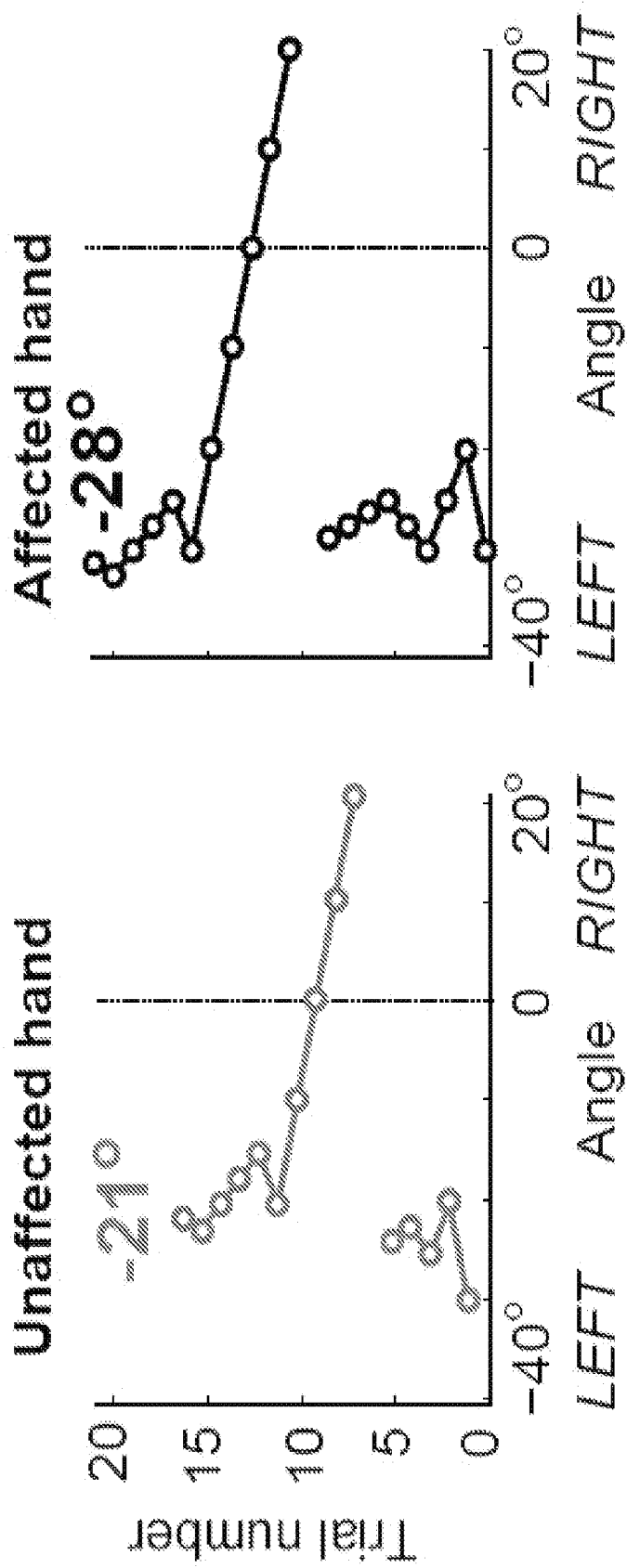
FIGS. 14A and 14B illustrate trial data from a stroke victim for both the unaffected hand and the affected hand respectively.
Figures 15A, 15B:
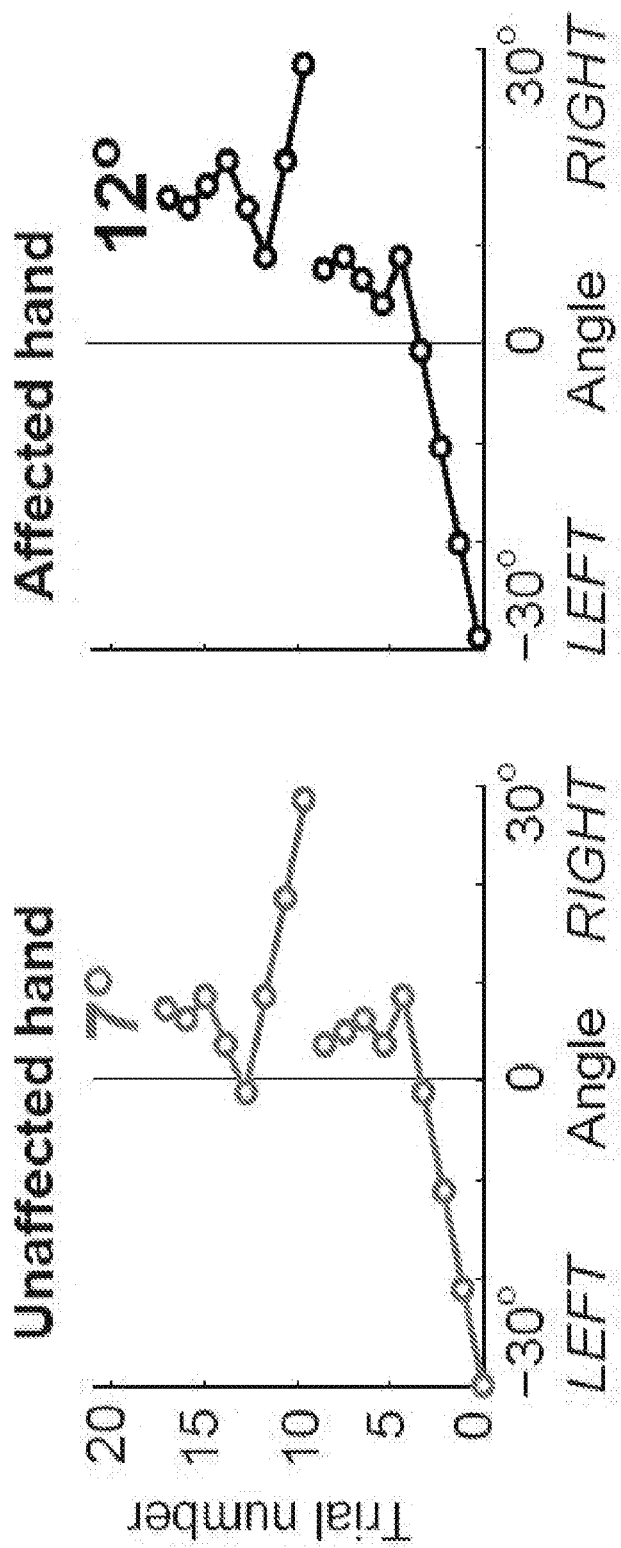
FIGS. 15A and 15B illustrate trial data from another stroke victim for both the unaffected hand and the affected hand respectively.
Figure 16B:
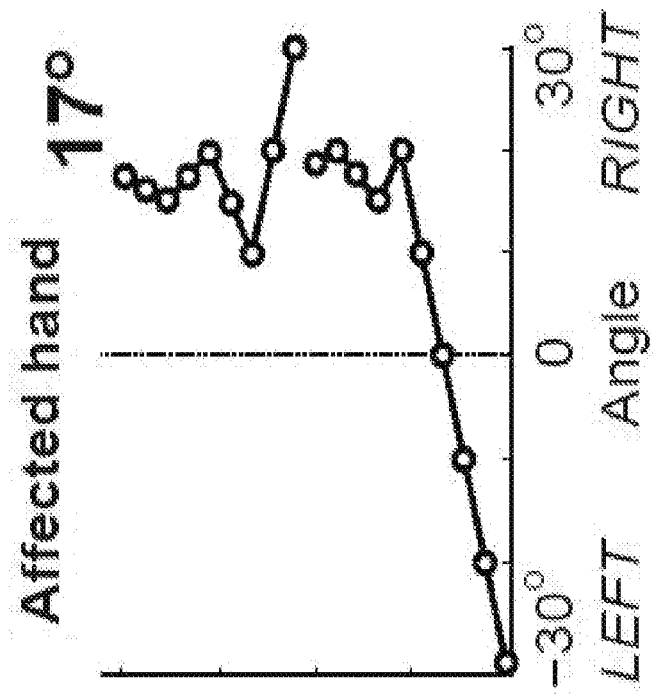
FIGS. 16A and 16B illustrate trial data from yet another stroke victim for both the unaffected hand and the affected hand respectively.
Figure 16A:
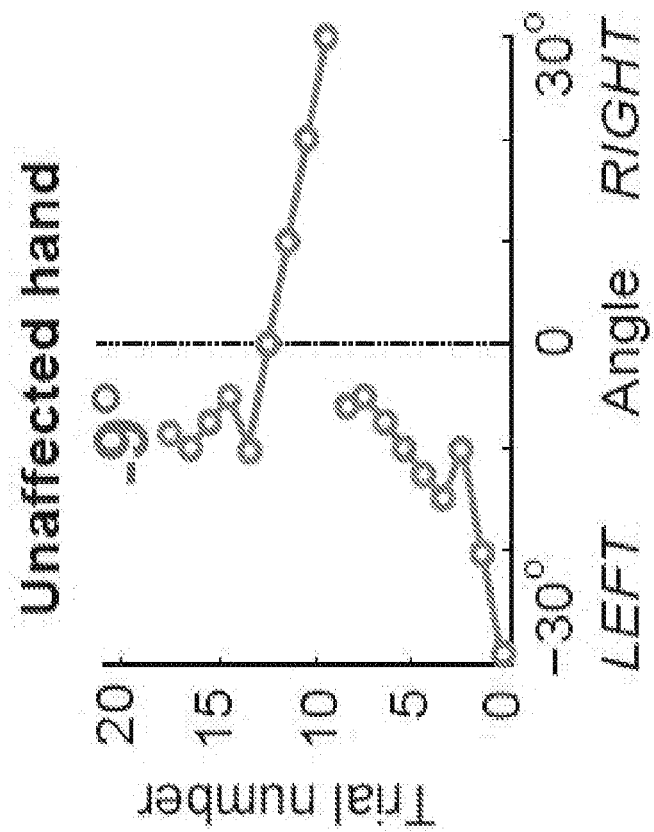

FIGS. 14A, 15A, and 16A illustrate data from three stroke victims for the unaffected hand, while FIGS. 14B, 15B, and 16B illustrate data from the same three stroke victims respectively for the affected hand. As can be seen in the comparison of FIGS. 14A with 14B, 15A with 15B, and 16A with 16B, the perceptual boundary is further from zero (there is worse proprioception) on the affected hand than there is for the unaffected hand. Thus, this data helps to illustrate that the embodiments disclosed herein are an effective tool of discriminating impaired proprioception in stroke victims where only one hand or side was affected by the stroke.

FIG. 17 is a table containing data for twelve individuals who had experienced ischemic or hemorrhagic strokes at least six months prior to testing. The following are explanations of the scores and abbreviations used therein:

FM thumb & index: Fugl Meyer assessment of proprioception. 2=normal, 1=moderately impaired, 0=severely impaired;

Fine touch level: lower is better;

FM UL: Fugl Meyer upper limb assessment of motor function (higher is better)

BBT: Box and Block Test of manual dexterity (higher is better)

MRC: Medical Research Council scale for muscle strength (5 is normal, lower is weaker)

MCA: middle cerebral artery CVA: cerebrovascular accident

Subjects were screened for cognitive impairment (MSSE>22) and hemi-spatial neglect (star cancellation score 0.46-0.54). The subjects were tested with the unaffected hand before the affected side was measured.

As can be seen in FIG. 17, some patients scored a 2 on the Fugl Meyer (FM) proprioception assessment for index finger and/or thumb on both sides, which may be interpreted as that according to that standard clinical measure, proprioception is fine on both hands. But, the tablet measurement, because it isn't a coarse rating scale like the FM, often shows different values for the two hands. Thus, embodiments disclosed herein may provide more effective and efficient means of determining the difference in proprioception between hands.

The tactile and motor measurements in FIG. 17 help to show that the measured subjects had substantial functional impairments in their affected hand even though they may have scored a 2 on the FM proprioception assessment.

While this disclosure has been described as having various exemplary designs, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements. The scope is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B or C may be present in a single embodiment; for example, A and B, A and C, B and C, or A and B and C.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art with the benefit of the present disclosure to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. § 112(f), unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method of measuring a patient's proprioception comprising:

placing a patient's hand at a predetermined position, without guided motion of the patient's hand toward the predetermined position, on an angled stand beneath a display screen with a portion of the patient's hand at a predetermined angle, wherein the stand comprises one or more raised portions configured to engage the patient's hand, facilitate proper placement of the patient's hand at the predetermined position, and separate an index finger of the patient's hand from a thumb of the patient's hand;

instructing a patient to apply pressure with the portion of the patient's hand that is at the predetermined position and predetermined angle and to not move the hand further;

displaying, by the display screen, before movement of the patient's hand from the predetermined position and while the patient's hand is at the predetermined position, a plurality of test positions; and receiving, from the patient, an indication of a positional relationship between an actual position of the portion of the patient's hand and each of the plurality of test positions on the display screen while the patient's hand is at the predetermined position.

2. The method of claim 1, wherein the displaying the plurality of test positions includes displaying varying test positions.

3. The method of claim 2, wherein the displaying the plurality of varying test positions comprises an adaptive staircase method.

4. The method of claim 3, further comprising determining a bias by averaging a plurality of reversal angles of the adaptive staircase method.

5. The method of claim 3, further comprising determining a proprioception sensitivity by determining a standard deviation of a plurality of reversal angles.

6. The method of claim 1, further comprising measuring and controlling the pressure of the portion of the patient's hand on the angled stand.

7. The method of claim 3, wherein an initial difference between the test position and the predetermined angle is about 30 degrees.

8. The method of claim 3, wherein a subsequent difference between the test position and the predetermined angle is 10 degrees.

9. The method of claim 1, wherein:
the method further comprises instructing the patient to move their hand toward the predetermined position on the stand, and to place their hand at the predetermined position with respect to the one or more raised portions on the stand.

* * * * *